US010761019B2

(12) United States Patent
Khodadad et al.

(10) Patent No.: US 10,761,019 B2
(45) Date of Patent: *Sep. 1, 2020

(54) ELECTROMAGNETIC WAVE EMITTANCE-BASED SPECIMEN ANALYSIS

(71) Applicant: Vital Biosciences Inc., Mississauga (CA)

(72) Inventors: Iman Khodadad, Toronto (CA); Alexander Wong, Waterloo (CA); Farnoud Kazemzadeh, Waterloo (CA)

(73) Assignee: VITAL BIOSCIENCES INC., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/248,238

(22) Filed: Jan. 15, 2019

(65) Prior Publication Data

US 2019/0219498 A1 Jul. 18, 2019

Related U.S. Application Data

(60) Provisional application No. 62/617,468, filed on Jan. 15, 2018, provisional application No. 62/630,946, filed on Feb. 15, 2018.

(51) Int. Cl.
*G01N 21/35* (2014.01)
*G01J 3/42* (2006.01)
(Continued)

(52) U.S. Cl.
CPC ......... *G01N 21/3563* (2013.01); *A61B 5/681* (2013.01); *A61B 5/6824* (2013.01);
(Continued)

(58) Field of Classification Search
CPC . A61B 5/0075; A61B 5/14546; A61B 5/1455; A61B 5/445; A61B 5/681;
(Continued)

(56) References Cited

U.S. PATENT DOCUMENTS

| 2004/0147034 | A1* | 7/2004 | Gore ................ A61B 5/14514 436/95 |
| 2004/0186361 | A1 | 9/2004 | Hwang et al. |
| 2014/0192342 | A1 | 7/2014 | Sass et al. |

FOREIGN PATENT DOCUMENTS

EP        1460413 B1     8/2006

OTHER PUBLICATIONS

International Search Report dated Apr. 26, 2019 as received in Application No. PCT/IB2019/050318.
(Continued)

*Primary Examiner* — Mark R Gaworecki
(74) *Attorney, Agent, or Firm* — Maschoff Brennan

(57) ABSTRACT

A method may include emitting a band of electromagnetic (EM) radiation towards a specimen that covers at least a first and a second wavelength of EM radiation. The method may also include receiving, at a first receiver configured to receive the first wavelength of EM radiation, responses to the EM radiation after the EM radiation interacts with the specimen; and receiving, at a second receiver configured to receive the second wavelength of EM radiation, responses to the EM radiation after the EM radiation interacts with the specimen. The method may also include extracting markers from a combination of first signals representative of the received responses at the first receiver and second signals representative of the received responses at the second receiver, the extracting including replicating and mixing the first signals and the second signals to extract the plurality of markers.

20 Claims, 8 Drawing Sheets

(51) Int. Cl.
    *G01J 3/02*     (2006.01)
    *G01J 3/36*     (2006.01)
    *G01J 3/28*     (2006.01)
    *G01J 3/10*     (2006.01)
    *G01N 21/25*     (2006.01)
    *A61B 5/00*     (2006.01)
    *G01N 21/3563*     (2014.01)
    *G01J 5/00*     (2006.01)
    *A61B 5/145*     (2006.01)
    *A61B 5/1455*     (2006.01)
    *G01J 3/453*     (2006.01)

(52) U.S. Cl.
    CPC .............. *G01J 3/0256* (2013.01); *G01J 3/10* (2013.01); *G01J 3/28* (2013.01); *G01J 3/36* (2013.01); *G01J 3/42* (2013.01); *G01J 5/0003* (2013.01); *G01N 21/255* (2013.01); *A61B 5/0075* (2013.01); *A61B 5/1455* (2013.01); *A61B 5/14546* (2013.01); *G01J 3/453* (2013.01)

(58) Field of Classification Search
    CPC ........ A61B 5/6824; G01J 3/0256; G01J 3/10; G01J 3/28; G01J 3/26; G01J 3/42; G01J 3/453; G01J 5/0003; G01N 21/255; G01N 21/3563
    See application file for complete search history.

(56) References Cited

OTHER PUBLICATIONS

Written Opinion of the International Searching Authority dated Apr. 26, 2019 as received in Application No. PCT/IB2019/050318.

* cited by examiner

US 10,761,019 B2

ELECTROMAGNETIC WAVE EMITTANCE-BASED SPECIMEN ANALYSIS

FIELD

The present disclosure relates in general to the field of electromagnetic (EM) wave emittance-based specimen analysis. For example, such analysis may be performed on bodily fluids, solutions, analytes, in vivo tissue, in vitro specimen, or other such specimens.

BACKGROUND

The human eye is capable of observing the visible wavelength ranges of the EM spectrum, which is a very small portion of the entire EM spectrum. If a broadband, "white" light source, such as the Sun, illuminates an object, that object would remit other wavelengths in addition to the visible wavelengths. Measuring certain characteristics of the remitted spectrum by an object can provide clues about the object's intrinsic properties.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

One or more embodiments may include a method that includes emitting a band of electromagnetic (EM) radiation towards a specimen, where the band of EM radiation covers at least a first and a second wavelength of EM radiation. The method may also include receiving, at a first receiver configured to receive the first wavelength of EM radiation and exclude the second wavelength of EM radiation, responses to the EM radiation after the EM radiation interacts with the specimen; and receiving, at a second receiver configured to receive the second wavelength of EM radiation and exclude the first wavelength of EM radiation, responses to the EM radiation after the EM radiation interacts with the specimen. The method may also include extracting markers from a combination of first signals representative of the received responses at the first receiver and second signals representative of the received responses at the second receiver, the extracting including replicating and mixing the first signals and the second signals to extract the plurality of markers.

One or more embodiments may include a system that includes an emitter configured to emit a band of radiation towards a specimen, the band including both a first wavelength of electromagnetic (EM) radiation and a second wavelength of EM radiation. The system may also include a first receiver configured to receive responses to the first wavelength of EM radiation after the first wavelength of EM radiation interacts with the specimen, and a second receiver configured to receive responses to the second wavelength of EM radiation after the second wavelength of EM radiation interacts with the specimen. The system may additionally include a signal mixer unit configured to extract markers from a combination of first signals representative of the received responses at the first receiver and second signals representative of the received responses at the second receiver, the extracting including replicating and mixing the first signals and the second signals to extract the markers.

One or more embodiments of the present disclosure may include a non-transitory computer-readable medium containing instructions that, when executed by a processor, are configured to cause a system to perform one or more operations. The operations may include to instruct an emitter to emit a band of electromagnetic (EM) radiation towards a specimen, the band including a first wavelength and a second wavelength of EM radiation. The operations may also include to receive, via a first receiver configured to receive the first wavelength of EM radiation and exclude the second wavelength of EM radiation, responses to the EM radiation after the EM radiation interacts with the specimen; and to receive, via a second receiver configured to receive the second wavelength of EM radiation and exclude the first wavelength of EM radiation, responses to the EM radiation after the EM radiation interacts with the specimen. The operations may additionally include to extract markers from a combination of first signals representative of the received responses at the first receiver and second signals representative of the received responses at the second receiver, the extracting including replicating and mixing the first signals and the second signals to extract the markers.

The object and advantages of the embodiments will be realized and achieved at least by the elements, features, and combinations particularly pointed out in the claims.

It is to be understood that both the foregoing general description and the following detailed description are merely examples and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
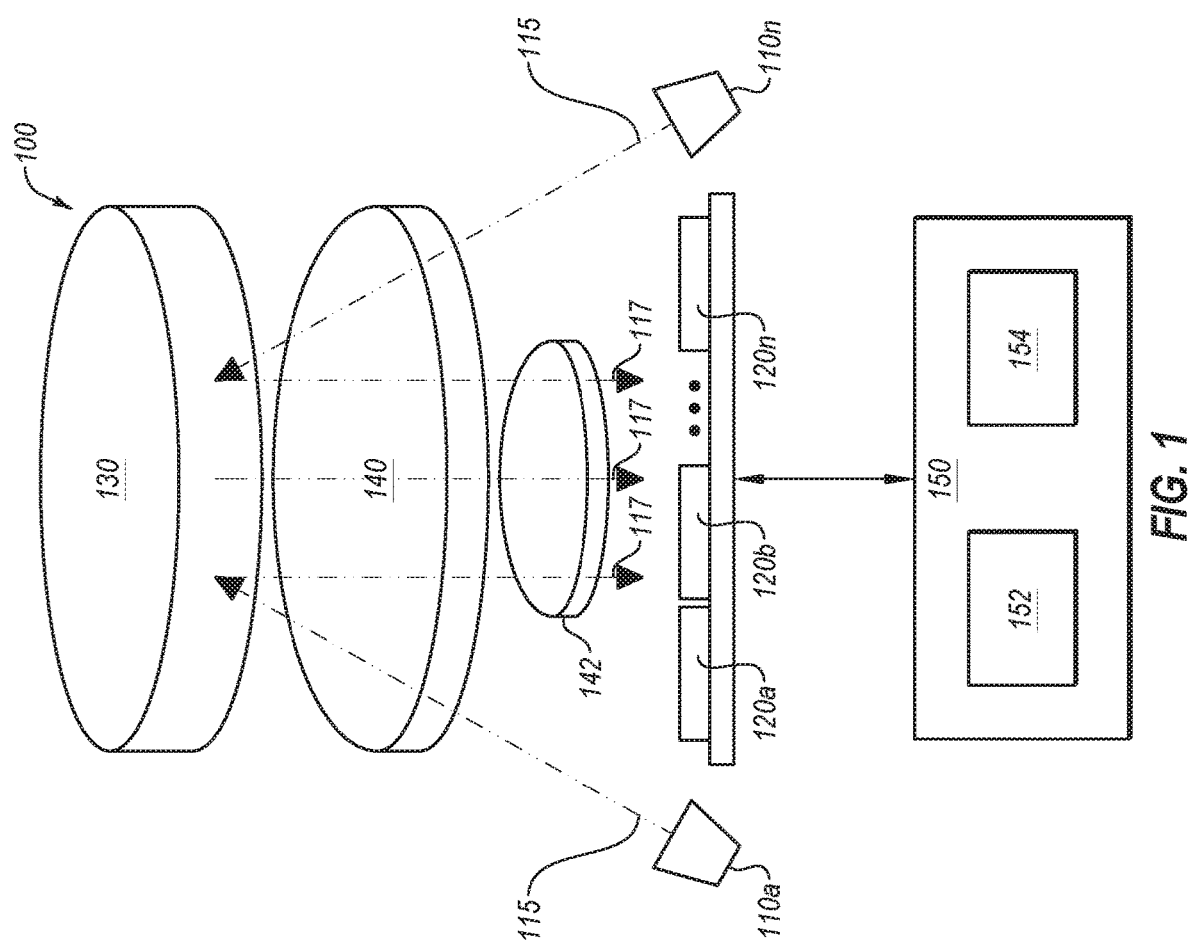
FIG. 1 illustrates an example system for imaging and/or analyzing a specimen.

In order to properly identify a state of a specimen, certain markers, which in combination can reliably and robustly represent that state, need to be identified and monitored. In many cases, due to natural variances inherent in the specimen being analyzed, individual markers may be smeared with noises within the received signal and one cannot deduce direct correlations with the state of the specimen being analyzed.

There are several approaches, such as multispectral (MS) or hyperspectral imaging, which are used for multi-band pass sensing. In case of imaging, one approach is to dissociate a color image, captured using a polychromatic camera, into its red, green, and blue (RGB) channels. This approach sub-divides the visible spectrum into three independent spectral bands. In such an approach, the spectral bands are highly dependent on the spectral response of the polychromatic sensor used for imaging and will vary between different sensors by different manufacturers. This approach is not a very accurate radiometric representation of targets within field-of-view (FOV) because polychromatic sensors typically use a Bayer filter to acquire the three channel RGB information and interpolate the missing spectral information in a given sensor pixel using its neighboring pixels, which do not necessarily contain similar spectral information.

One alternative approach to multi-spectral imaging employs a series of spectral bandpass filters combined with a monochromatic camera. These filters are designed to accurately transmit a wavelength range of interest while suppressing all other wavelengths. The filters can be placed in the path of the light entering the camera using approaches like a motorized filter wheel, liquid-crystal tunable filters, or acousto-optical tunable filters. Another alternative approach uses a series of light sources that can illuminate the target with light of a specific wavelength range. In this alternative approach, the remitted light is acquired on a monochromatic camera.

Some approaches perform simultaneous imaging for multi-spectral imaging using various beam splitter arrangements such that each spectral region may be imaged on its own respective camera system. Some approaches use a handheld MS imager that is limited to performing imaging in very limited spectral bands, such as the visible and the near-Infrared (NIR) spectral range. However, these systems only operate in the visible or in the NIR spectral range and are typically bulky and large. Other MS based imaging approaches are limited to the discrete EM spectrum of either the light sources or the sensor filters and therefore limited in the number of data points that can be accessed, processed, and extracted.

Additionally, such approaches use large imaging sensors or three-color photo detectors to perform the colorimetry. Such approaches are limited in accuracy since they only use three primary colors for read out from one broadband source or a few narrow-band sources. In other circumstances, only one or a few filters with narrow band pass are used to read each signature response in sequence. In addition, due to the bigger implementation size and discrete components, such approaches are limited in application and are only able to take measurements at discrete and limited points of time. Additionally, in certain applications and conditions, continuous monitoring of certain markers may be beneficial and meaningful to identify and follow a useful course of response. In addition, instantaneous measurement of a number of variables at the same time may be valuable in order to correlate such variables with certain physiological states. Additionally, the analysis of multiple inter-related markers simultaneously may be unavailable using traditional analysis techniques. The present disclosure may provide systems and methods that may facilitate the analysis of multiple inter-related markers simultaneously.

The present disclosure relates to methods and systems for exposing a specimen to various wavelengths of EM radiation and analyzing the responses to the EM radiation interacting with a specimen for analysis. Signals representative of the initial EM radiation and/or the received responses to the EM radiation after interacting with the specimen may be provided to a replicating and/or mixing device to extract markers from the signals. The markers may be compared to a known set of markers to determine a state of the specimen. For example, a user may wear a device that exposes skin tissue to EM radiation and determines a physiological state of the user based on the analysis. As another example, the user may use the device on bodily fluids such as a drop of blood or urine to determine their health status.

Embodiments of the present disclosure improve upon such previous approaches. Such embodiments are explained with reference to the accompanying drawings.

FIG. 1 illustrates an example system 100 related to imaging and/or analyzing a specimen, in accordance with one or more embodiments of the present disclosure. The system 100 may include one or more emitters 110 (such as the emitters 110a and 110n), one or more receivers 120 (such as the receivers 120a, 120b, and 120n), and a signal mixer unit 150. The emitters 110 may emit EM radiation 115 towards a specimen 130 to be analyzed, and the receivers 120 may receive the responses to the EM radiation 117 based on the EM radiation interacting with the specimen 130. One or more amplifying devices 140 and/or 142 may amplify the EM radiation 115 before interacting with the specimen 130, and/or may amplify the responses to the EM radiation 117 after interacting with the specimen 130. The signal mixer unit 150 may perform processing on the signals generated by the receivers 120 based on the EM radiation interactions and/or on the signals of the EM waveforms emitted by the emitters 110. The signal mixer unit 150 may include a mixing and replicating device 152 for extracting markers from the received signals, and/or a comparison device 154 for comparing the markers extracted by the mixing and replicating device 152 with known sets of markers.

The emitters 110 may include any system, device, or component configured to emit a band of EM radiation. The band of EM radiation may include any range of EM radiation, such as radio waves, microwaves, infrared (IR) waves, visible light, ultraviolet (UV) light, x-rays, gamma rays, terahertz waves, etc. In some embodiments, the emitters 110 may include multiple emitters, where different emitters 110 are configured to emit radiation at different wavelengths, and may be independently excited to emit the radiation. Additionally or alternatively, the emitters 110 may be tunable or otherwise adjustable such that a single emitter 110 may be configured to emit multiple different wavelengths at different times (or at the same time).

In some embodiments the emitters 110 may include time interleaved independent band limited sources of EM radiation, and/or an extended bandpass source. For example, if three emitters are utilized with three distinct bands of EM radiation, the emitters may be sequentially powered to emit their respective bands of EM radiation and the target response to be detected by the receivers 120. Additionally or alternatively, the emitters 110 may all be powered at the same time to emit the three bands of EM radiation simultaneously. In these and other embodiments, the combination of the emitters 110 may provide the expected excitation EM radiation that interacts with the specimen 130. The expected EM radiation may be represented by:

$$S(f) = S_0(f_0) + S_1(f_1) + \ldots + S_k(f_k)$$

where each emitted field $S_i(f_i)$ may represent the EM field emanating from the $i^{th}$ emitting source at frequency $f_j$ having a specific bandpass domain. In some embodiments, the emitters 110 may have sufficient power to interact with the specimen 130 and scatter back a response to be received at the receivers 120. In some embodiments, the emitters 110 may provide any form of spatial radiation such as tophat, Bessel, Gaussian, etc.

The receivers 120 may include any system, device, or component configured to detect EM radiation and transduce the incoming radiation into a readable signal representative of the EM radiation detected. In some embodiments, the receivers 120 may include multiple receivers 120 where each receiver is configured to receive different wavelengths of EM radiation (e.g., narrow band receivers). Additionally or alternatively, a single receiver may be configured to detect radiation at multiple wavelengths (e.g., wide band receivers). In some embodiments, one or more of the receivers 120 may utilize a filter or other mechanism such that the signal detected by the receivers 120 is representative of a specific band of wavelengths, rather than all wavelengths of EM radiation received by the receiver. Such filters may be tunable or may be static filters.

In some embodiments, the EM radiation detected by the receivers 120 may be represented by:

$$D(f)=D_0(f_0)+D_1(f_1)+ \ldots +D_i(f_j)$$

where the target location $D_i(f_j)$ may represent the EM field detected by the $i^{th}$ receiver at frequency $f_j$.

In some embodiments, the receivers 120 may include an imaging sensor with charged coupled devices (CCD), complementary metal oxide semiconductor (CMOS) pixels, or photodiodes. In one embodiment, the receivers 120 may utilize discrete filters to provide band passes over the detecting radiation. The combination and placement of such filters on the receivers 120 in addition to the time interleaved sources may provide the basis to the signal mixer unit to produce a non-sparse interaction response (e.g., the signal used for estimation of status of the target). In some embodiments, the receivers 120 may include any form of an antenna that receives the EM signals in specific locations and/or at specific angles.

In some embodiments, the combination of receivers 120 (e.g., the receivers 120a-120n) may be micro-patterned (e.g., arranged in a pattern that is small in size and/or small in number of receivers 120) and packaged together into a very small form factor, such as on the order of millimeters or centimeters in size, such as less than ten square centimeters, less than three square centimeters, or less than one square centimeter in size. In some embodiments, the form factor may be one inch by two inches in size. In these and other embodiments, the combination of receivers 120 may receive the response from the specimen 130 at multiple bands of wavelengths of EM radiation at the same time. For example, the combination of receivers 120 may be implemented as an array of photodiodes with specific band pass filters.

The specimen 130 may include any material, tissue, fluid, assay, etc. to be imaged and/or analyzed. One example of the specimen may 130 include skin tissue, whether in vivo, in vitro, ex vivo, in situ, etc. Another example of the specimen 130 may include other human tissue. An additional example of the specimen may include bodily fluids, such as blood, saliva, sweat, urine, mucus, tears, semen, vaginal secretion, vaginal discharge, breast milk, pus, bile, amniotic fluid, cerebrospinal fluid, gastric acid, cerumen (earwax), etc. Another example of the specimen 130 may include a chemical solution, including, a chemical solution undergoing a reaction, a liquid homogenate of hair, etc. In some embodiments, the specimen 130 may be part of a living entity. In some embodiments, the specimen 130 may be a fluid disposed within a storage container or other receptacle. In some embodiments, the specimen 130 may be disposed on a medium to facilitate analysis, such as a glass slide, petri dish, etc.

In some embodiments, the system 100 may utilize one or more amplifying devices 140 and/or 142. The amplifying device 140 may be configured to amplify the EM radiation 115 before it arrives at the specimen 130. The amplifying device 142 may be configured to amplify the response to EM radiation 117 after it has interacted with the specimen 130. Additionally or alternatively, the amplifying device 142 may focus and/or localize the responses to the EM radiation 117 towards the receivers 120. In these and other embodiments, the amplifying devices 140 and/or 142 may include any combination of focusing systems, such as lens focusing systems, metamaterial focusing systems, nanowire and/or nano-structure based focusing systems, aqueous based non antennas, substrate based nano-antennas, pumped lasing systems, spontaneous and/or stimulated emission systems, etc. By using one or both of the amplifying devices 140 and/or 142, a signal to noise ratio (SNR) may be improved. Additionally or alternatively, the amplifying devices 140 and/or 142 may permit the use of certain types of emitters 110 that may not be viable without amplification.

The signal mixer unit 150 may include any system, device, or component configured to perform processing on the signals detected by the receivers 120. In some embodiments, the signal mixer unit 150 may include a computing device (such as the computing device illustrated in FIG. 8). The signal mixer unit 150 may include the mixing and replicating device 152 for extracting markers from the received signals, and/or the comparison device 154. Examples of one or more components of the signal mixer unit 150 may be illustrated in FIGS. 3 and/or 4.

In some embodiments, the signal mixer unit 150 may be implemented as an integrated circuit, as a look-up table function, or as various adaptive mixing circuitries such as digital signal processing units, field programmable arrays, optical holographic units, etc. The implementation of the signal mixer unit 150 may take various forms and is not limited to a certain architecture or hardware.

In some embodiments, the mixing and replicating device 152 may be configured to replicate and mix the signals of the receivers 120 to generate a spatio-spectral response as detected by the receivers 120 that may be time-interleaved. For example, the spatio-spectral response may include values representative of the response of the specimen 130 to the EM radiation emitted by the emitters 110 and as detected by the receivers 120 across multiple spectral bands of EM radiation and across the spatial regions of the arrangement of the receivers 120.

In some embodiments, the mixing and replicating device 152 may utilize data or signals related to the receivers 120 and/or the emitters 110. For example, the mixing and replicating device 152 may include a layer of replicator units followed by a layer of mixer units (which may be repeated in cascade any number of times). In these and other embodiments, the time interleaved emitter 110 signals and the spatially and spectrally interleaved responses detected by the receivers 120 may be replicated and mixed to produce spatio-spectral responses from each or a combination of the individual receivers 120. Stated another way, the mixing and replicating device 152 may be configured to use a combination of signals from time-multiplexed emitters 110 and signals from the spatio-spectral receivers 120 to produce a spatio-spectral matrix response from the specimen 130. In these and other embodiments, the output of the mixing and replicating device 152 may be the extracted markers associated with the specimen 130. The extracted markers may correspond to a property of interest being analyzed in the specimen, such as a target chemical component within the specimen 130, or a physiological state of the specimen 130, or some other parameter, the combination of which indicates a state of the specimen.

In operation, a replicator unit of the mixing and replicating device 152 may utilize an input signal and replicate it a multitude of times to produce output signals to feed into a set of mixer units. A mixer unit may utilize a set of input signals and perform mixing based on a mixing function to produce an output signal. In these and other embodiments, a mixing function (f) used by a signal mixer unit of the mixing and replicating device 152 may be represented by $$f(x_1, x_2, \ldots, x_p) = a_1 x_1^{b_1} l + a_2 x_2^{b_2} + \ldots + a_p x_p^{b_p}$$

where $a_i$ and $b_i$ are parameters corresponding to the $i^{th}$ input signal, and $x_1, x_2, \ldots, x_p$ may represent the $i^{th}$ input signal.

In some embodiments, the parameters of the mixing and replicating device 152 may be tuned based on the desired application. For example, if imaging skin and analyzing for skin disease, the markers may include any of physiological markers, concentrations of deoxygenated hemoglobin, oxygenated hemoglobin, bilirubin, carotenes, eumelanin, pallor of skin, skin pigmentation, etc. and the parameters may be tuned accordingly. As another example, if imaging a chemical assay or biological fluid, the markers may include any of physiological markers, concentration of a drug (e.g., THC, cocaine, amphetamines, ketamine, ecstasy, opiates, alcohol, nicotine, etc.), other organic and/or inorganic compounds, other constituents of bodily fluids, hormones, proteomes, primary metabolites, molecular conjugates, protein biomarkers, protein fragments, organic contaminants, inorganic contaminants, endogenous ions, heavy metals, genes, small molecules of interest, etc. Additionally or alternatively, if imaging a biological fluid, the markers may include the presence or absence of an infectious pathogen, such as bacteria or viruses. In these or other embodiments, the markers may include the absence or presence of certain cells or cell types, cell surface markers, proteins, nucleic acid fragments, etc. that may indicate the type or serotype of an infectious pathogen. Additionally or alternatively, the presence or concentration of naturally occurring compounds like cortisol may be monitored. As a further example, the presence of nutrition/health based compounds may be monitored, such as vitamins (e.g., vitamin B, C, E, etc.) and minerals (e.g., Zinc, Iron, etc.).

In some embodiments, after extracting the markers at the mixing and replicating device 152, the markers may be provided to the comparison device 154. The comparison device 154 may include any system, device, circuitry, or other components configured to compare one or more markers with one or more known sets of markers to facilitate determination and/or prediction of a state of the specimen 130. For example, known concentrations of compounds within an analyte, or tissue samples with known conditions, etc. may be analyzed and the corresponding markers may be stored in a look-up table or other storage medium such that the extracted markers from the mixing and replicating device 152 may be compared by the comparison device 154 to such previously known sets of markers. In these and other embodiments, the comparison device 154 may be implemented as an integrated circuit with a lookup table function, as various adaptive mixing circuitries such as digital signal processing (DSP) units, field programmable gate arrays (FPGAs), etc.

The system 100 may operate in any of a variety of circumstances. For example, the system 100 may be utilized to analyze bodily fluids (such as blood, saliva, sweat, etc.), liquid homogenates of hair, chemical solutions, etc., whether in vitro, in vivo, or ex vivo. In analyzing such fluids/solutions, the system 100 may monitor for the presence of drugs or alcohol, etc. When the system 100 operates as a device to monitor for illicit drugs, alcohol, etc., the system 100 may monitor for intoxication, for example, at a roadside stop by law enforcement. As an additional example, the system 100 may monitor for certain compounds associated with stress or fatigue in mission critical situations (e.g., monitoring for Cortisol by analyzing saliva of an astronaut). As another example, the system 100 may be utilized for analyzing skin of a user, such as analysis of subcutaneous physiological markers to determine health of the user. As another example, the system 100 may be utilized for analyzing a drop of blood from skin to monitor for hormone levels and/or presence or absence of certain targets.

In analyzing skin of a user, certain benefits may be obtained. For example, skin color may reflect overall health of a patient, and may be a useful tool in assessing skin breakdown, wound healing, cardiovascular diseases, nutritional deficiencies, etc. In analyzing skin color, pallor may indicate whether or not the user has anemia; cyanosis may signal hypoxemia, and the degree and extent of skin redness may be indicative of cardiovascular malfunctions.

Understanding skin-color changes may be beneficial for detecting and staging pressure ulcers, physiological changes, etc. However, the exact nature of such color changes as pallor, cyanosis, and redness varies with the natural skin color of the user which may pose a challenge in providing clinically competent care. For example, many skin-care guidelines apply mainly to users with light skin, and so are inapplicable and may make it difficult to detect skin color changes for individuals of different ethnic backgrounds and skin colors. In such a context, detection of skin color changes on different background pigments may be beneficial using the system 100.

In this regard, constitutive skin color is the natural, genetically determined color of the epidermis, uninfluenced by ultraviolet (UV) light or hormone exposure. Typically, such skin color is seen in areas of little or no sun exposure, such as the underside of the upper arm. In contrast, facultative skin color results from exposure to UV light and other environmental factors. Tanning, for instance, changes the composition of melanin in the skin and increases the amount and size of melanin produced by melanocytes. Thus, facultative skin is darker than constitutive skin. Skin color of a user is the result of reflected and absorbed light from unpigmented skin, mixed with colors of various constitutive pigments, such as melanins, hemoglobins, and carotenes. Therefore, one can assess both properties of unpigmented skin as well as its constitutive pigments to assess and predict various states and conditions.

In addition, other conditions such as Erythema may be hard to detect in dark-skinned patients. In a light-skinned patient, irritation may cause redness. But in a dark-skinned person, it may cause hyperpigmentation (increased pigmentation) or hypopigmentation (reduced pigmentation), with no redness visible. Therefore, robust and continued monitoring of skin, such as provided by embodiments of the present disclosure, may be beneficial in detecting physiological changes within a user's body, and within the area that the measurement is taken, in a manner beneficial to light-skinned or darker-skinned patients.

In these and other embodiments, analysis according to the present disclosure may occur in real-time and may be continuous such that the skin of the user may be monitored for pallor, skin color changes, etc. For example, the system 100 may be implemented as a wearable device on the wrist of a user, around the arm of a user, etc. In these and other embodiments, the system 100 may non-invasively monitor and/or analyze various aspects of a user by analyzing the skin.

In some embodiments, the system 100 may perform the imaging and/or analysis in a rapid time frame. For example, the system 100 may obtain the sample, emit the band of radiation, and extract the markers within a limited time frame. The limited time frame may include approximately less than fifteen minutes, less than eleven minutes, less than eight minutes, less than three minutes, less than one minute, or less than thirty seconds. In some embodiments, a number of iterations of cascades within the signal mixer unit 150 may be limited to facilitate a more rapid analysis and/or extraction of the markers.

In some embodiments, the system 100 may be implemented with a very small form factor, such as being implemented as a wearable and/or portable device. In some embodiments, the system 100 may weigh less than fifteen pounds, less than ten pounds, less than eight pounds, less than five pounds, or less than one pound. In these and other embodiments, the system 100 may be used for continuous monitoring of one or markers the system 100 is intended to monitor. For example, the measurement unit may be situated in-situ for continuous monitoring of the target specimen (such as by placing the system 100 within a reaction vessel to continuously monitor for the decrease of a reagent or the appearance of a product during a chemical reaction). In these and other embodiments, continuous monitoring may facilitate analysis in real-time of various physiological parameters and/or phenomena. Additionally or alternatively, events or conditions that may be transient or may vary over time may be monitored for and analyzed, including generating a time-resolution analysis of the event or condition.

In these and other embodiments, the totality of the emitters 110, receivers 120, certain variations of the amplification devices 140 and/or 142, and/or the signal mixer unit 150 may be integrated on a single, portable (e.g., for roadside traffic stops) and/or wearable (e.g., worn around the wrist) form factor using rechargeable power sources (such as a battery) for field use and/or monitoring of users. After the interaction of the emitted EM radiation 115 with the specimen 130, the scattered EM radiation 117 response may be sensed by the receivers 120. The signals generated by the receivers 120 may be fed into the signal mixer unit 150 to extract the respective markers. The signal mixer unit 150 may have many implementations such as any form of field programmable gate arrays, digital signal processing units, graphical processing units, any generalized central processing units or optical/RF wavelength division multiplexing (WDM) units.

In some embodiments, the system 100 may be used by prosumers, consumers, and/or at risk people for the purpose of detecting abnormalities using the markers manifested within their skin and/or bodily fluids. In one embodiment, the device can be used to continuously monitor the skin pigmentation to measure and monitor for cutaneous inflammatory diseases, cholesterol embolism (which is highly suspected in patients with known atherosclerotic disease and a classic history of renal failure), abdominal pain, livedo reticularis, etc. Other cases include, but are not limited to, detecting metabolic syndrome (which is a risk factor for coronary heart diseases), as well as diabetes, fatty liver, and several cancers; pallor level in patients with mechanical heart valve disorders and other cardiovascular disorders, etc. In these and other embodiments, the system 100 may be used to monitor for hormone levels, disease or dysfunctions of internal organs or cells, presence or absence of parasites, bacteria or viruses, etc., through intermediary bodily fluids.

In some embodiments, after extracting the markers and/or determining a state of the specimen 130, the system 100 may communicate the state and/or markers to another device, such as an electronic device of a user (not illustrated), an electronic device of a medical professional (not shown), etc. In these and other embodiments, the state and/or markers may be compared to a threshold or other monitored value and may trigger an alert or alarm based on passing the threshold. The alerts or alarms may be presented to the user visually (e.g., a light that is illuminated or a display on a screen), audibly (e.g., with a chime or siren sound), via software (e.g., on a mobile device application message). In some embodiments, such an alert or alarm may invoke an emergency response, such as dialling 9-1-1, sending an automated message to a medical professional, causing the delivery of a medication, turning on a medical device, etc.

Modifications, additions, or omissions may be made to FIG. 1 without departing from the scope of the present disclosure. For example, the system 100 may include more components or fewer components than those illustrated.

Figure 2:
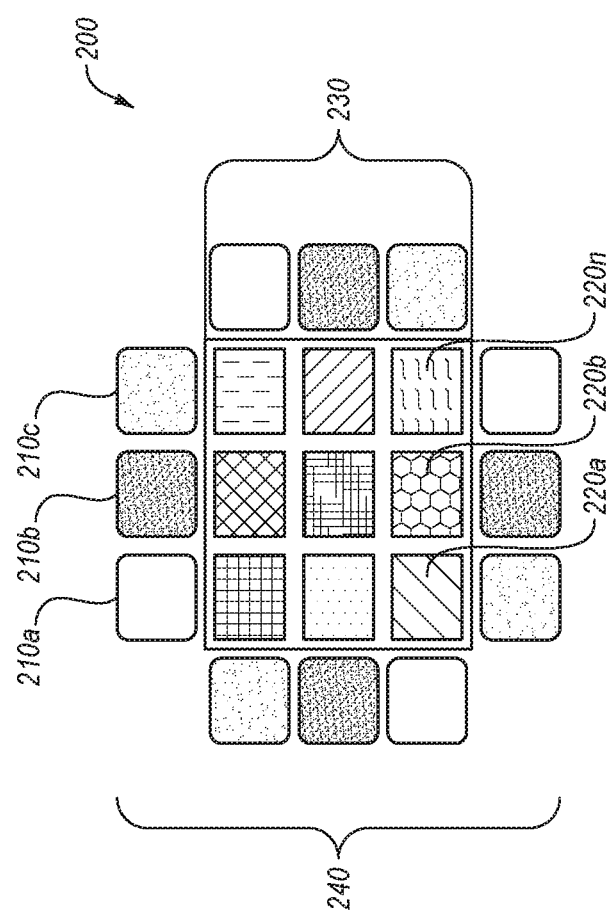
FIG. 2 illustrates one example arrangement of emitters and receivers to facilitate imaging and/or analyzing of a specimen.

FIG. 2 illustrates one example arrangement 200 of emitters 210 (such as the emitters 210a-210c) and receivers 220 (such as the receivers 220a-220n) to facilitate imaging and/or analyzing of a specimen, in accordance with one or more embodiments of the present disclosure.

As illustrated in FIG. 2, in some embodiments, the emitters 210 may include a first emitter 210a configured to emit radiation at a first band of EM radiation, a second emitter 210b configured to emit radiation at a second band of EM radiation, etc. In these and other embodiments, the receivers 220 may include a first receiver 220a configured to detect EM responses at a first wavelength, a second receiver 220b configured to detect radiation at a second wavelength, etc. The various hashmarks illustrate that the various emitters 210 and/or receivers 220 may be configured to operate at a particular spectral, temporal, and/or polarized sequence, or some portion or any combination of any of the foregoing.

In some embodiments, the receivers 220 may be positioned in a central region 230 that may correspond generally with the specimen. For example, the specimen may be positioned relative to the receivers 220 such that as EM response is scattered off of the specimen it is directed back towards the receivers 220.

In some embodiments, the emitters 210 may be positioned in an outer region 240 that goes around the central region 230.

While one embodiment is illustrated in FIG. 2, it will be appreciated that any arrangement of emitters 210 and receivers 220 are contemplated within the present disclosure. For example, the emitters 210 and the receivers 220 may be interspersed among each other. As another example, the emitters 210 may be in the central region 230 and the receivers 220 may be in the outer region 240. As an additional example, a smaller and/or larger number of emitters 210 and/or receivers 220 are contemplated.

Modifications, additions, or omissions may be made to the system 200 without departing from the scope of the present disclosure. For example, any number of arrangements of emitters 210 and receivers 220 are contemplated.

Figure 3:
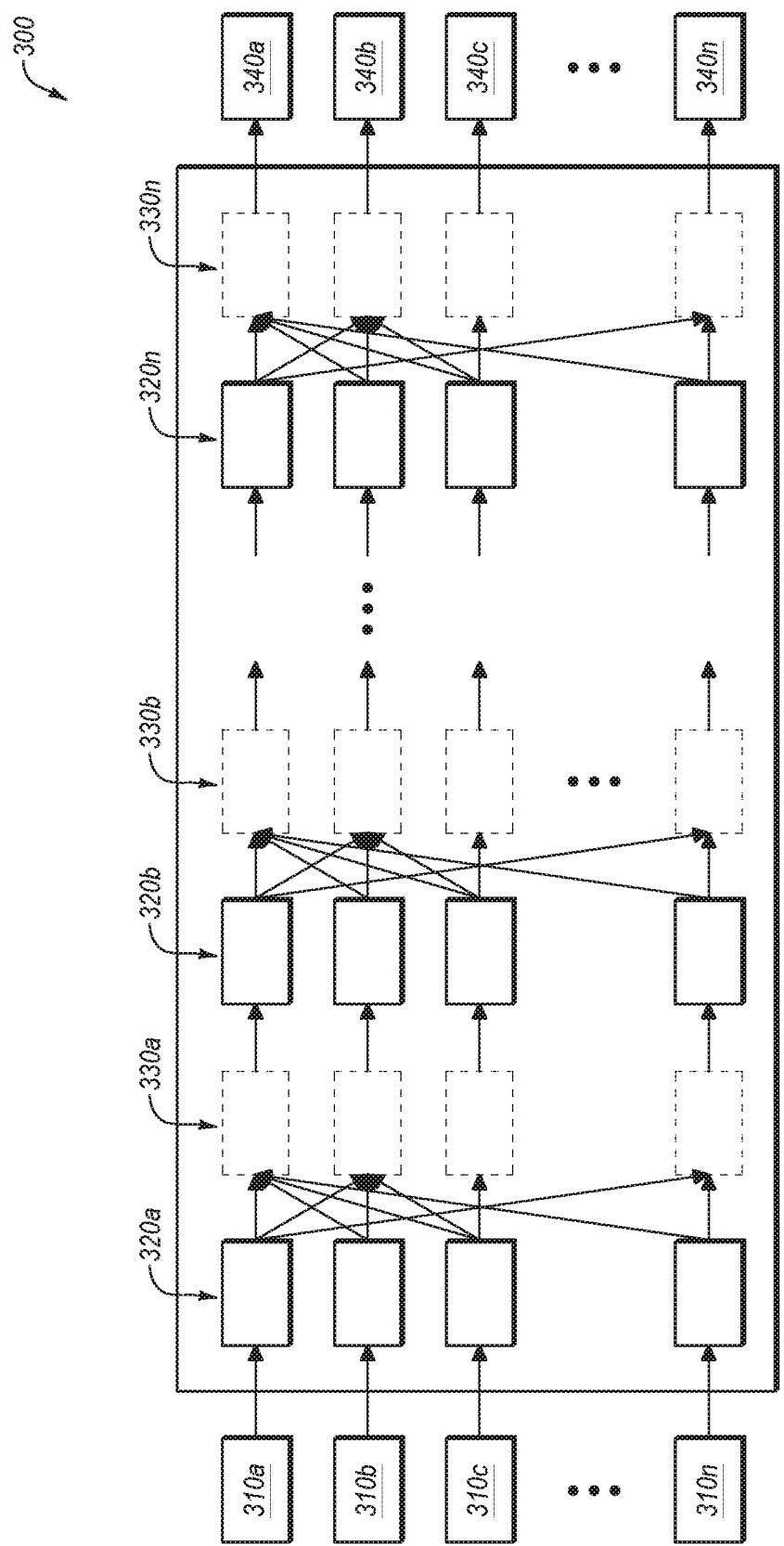
FIG. 3 illustrates an example of a signal mixer device that may operate on received EM radiation after interacting with a specimen.

FIG. 3 illustrates an example of a signal mixer device 300 that may operate on responses to the EM radiation after interacting with a specimen as received at receivers, in accordance with one or more embodiments of the present disclosure. As illustrated in FIG. 3, the signal mixer device 300 may receive as input one or more of the received signals 310 (e.g., received signals 310a, 310b, . . . , 310n) as detected by the receivers and/or as emitted by the emitters and interacting with the target. The signal mixer device 300 includes a first set of replicators 320a that replicate the input signals a number of times and pass those signals to one or more mixer unites 330a. The output of the mixer units 330a may be used as the input signal for the next cascade of replicators 320b. The output of the replicators 320b may be used as the inputs for the mixer units 330b. While three iterations of the cascade of replicators 320 and mixers 330 are illustrated, any number of iterations of replicators 320 and mixers 330 (e.g., up to the replicators 320n and mixers 330n) are contemplated within the present disclosure.

After the cascade of replicators 320 and mixers 330, the signal mixer device 300 may output a series of spectro-spatial responses 340a-n. In some embodiments, the outputs 340 may correspond to the markers being analyzed. In some embodiments, the number of spectro-spatial responses 340 may be based on the number of frequency bands emitted, the number of frequency bands selected for by the receivers, the number of distinct spatial signals received, the number of receivers, the number of emitters, the combination set of emitters emitting at a subset of bands at the same time, etc. Additionally or alternatively, the number of responses 340 may correspond to the number of markers or parameters being analyzed and/or considered.

Modifications, additions, or omissions may be made to the signal mixer device 300 without departing from the scope of the present disclosure. For example, any number of iterations of the cascade of replicators 320 and mixers 330 may be included.

Figure 4:
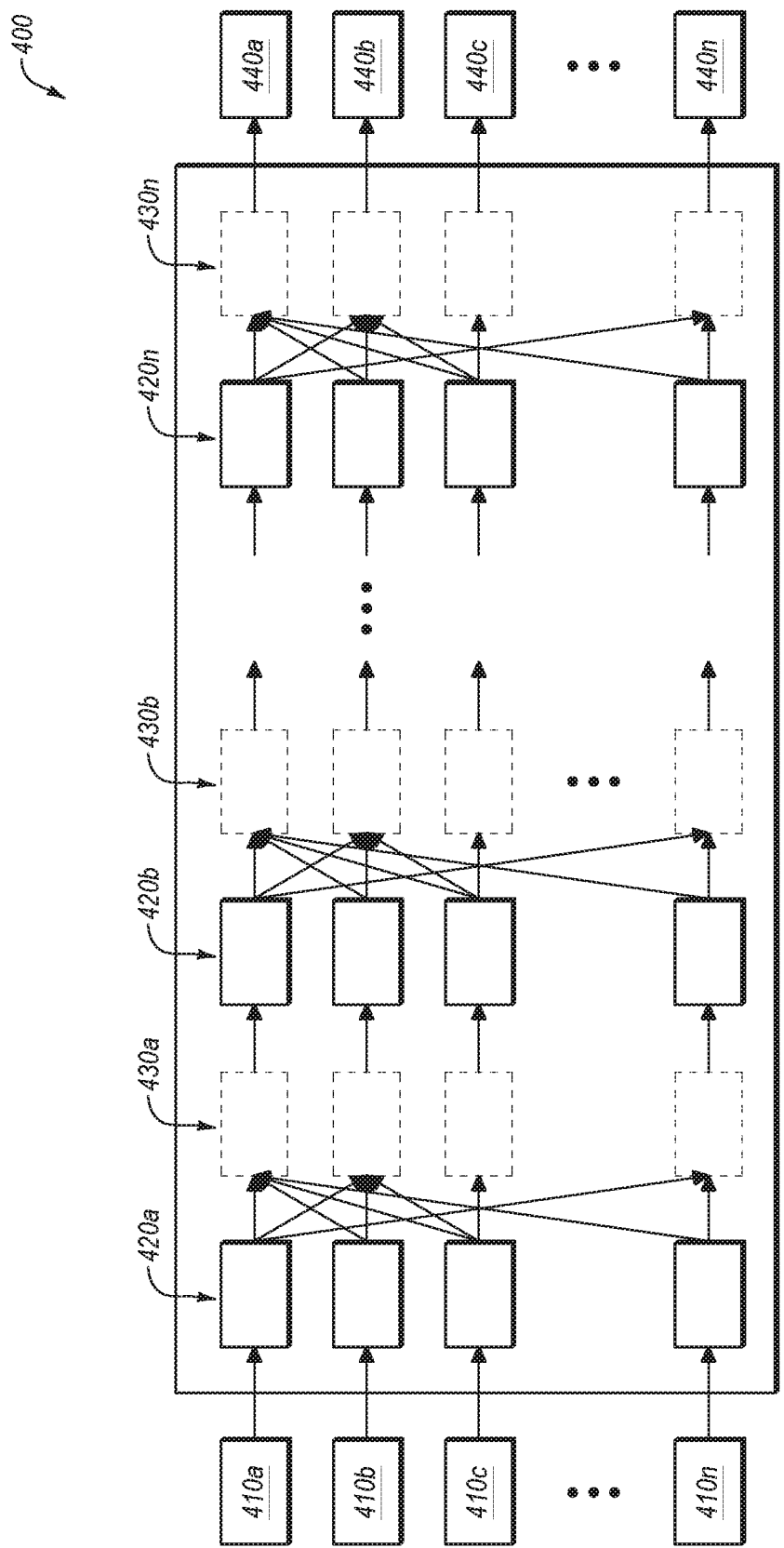
FIG. 4 illustrates an example of a signal mixer device that may operate on emitted EM waveforms.

FIG. 4 illustrates an example of a signal mixer device 400 that may operate on emitted EM waveforms, in accordance with one or more embodiments of the present disclosure. As illustrated in FIG. 4, the signal mixer device 400 may receive as input the EM waveforms used by the emitters when emitting EM radiation (e.g., the EM waveforms used by the emitters 110 of FIG. 1). The signal mixer device 400 includes a first set of replicators 420a that replicate the input signals a number of times and pass those signals to one or more mixer units 430a. The output of the mixer units 430a may be used as the input signal for the next cascade of replicators 420b. The output of the replicators 420b may be used as the inputs for the mixer units 430b. While three iterations of the cascade of replicators 420 and mixers 430 are illustrated, any number of iterations of replicators 420 and mixers 430 (e.g., up to the replicators 420n and mixers 430n) are contemplated within the present disclosure.

After the cascade of replicators 420 and mixers 430, the signal mixer device 400 may output a set of waveforms 440 (such as the waveforms 440a-440n) as mixed spatially and/or temporally. In these and other embodiments, the waveforms 440a-440n may be utilized by a signal mixer device operating on the signals representative of the received EM radiation (e.g., the signal mixer device 300 of FIG. 3) to facilitate the comparison of the received signals with the EM radiation waveform utilized to emit radiation.

Modifications, additions, or omissions may be made to the signal mixer device 400 without departing from the scope of the present disclosure. For example, any number of iterations of the cascade of replicators 420 and mixers 430 may be included.

Figure 5:
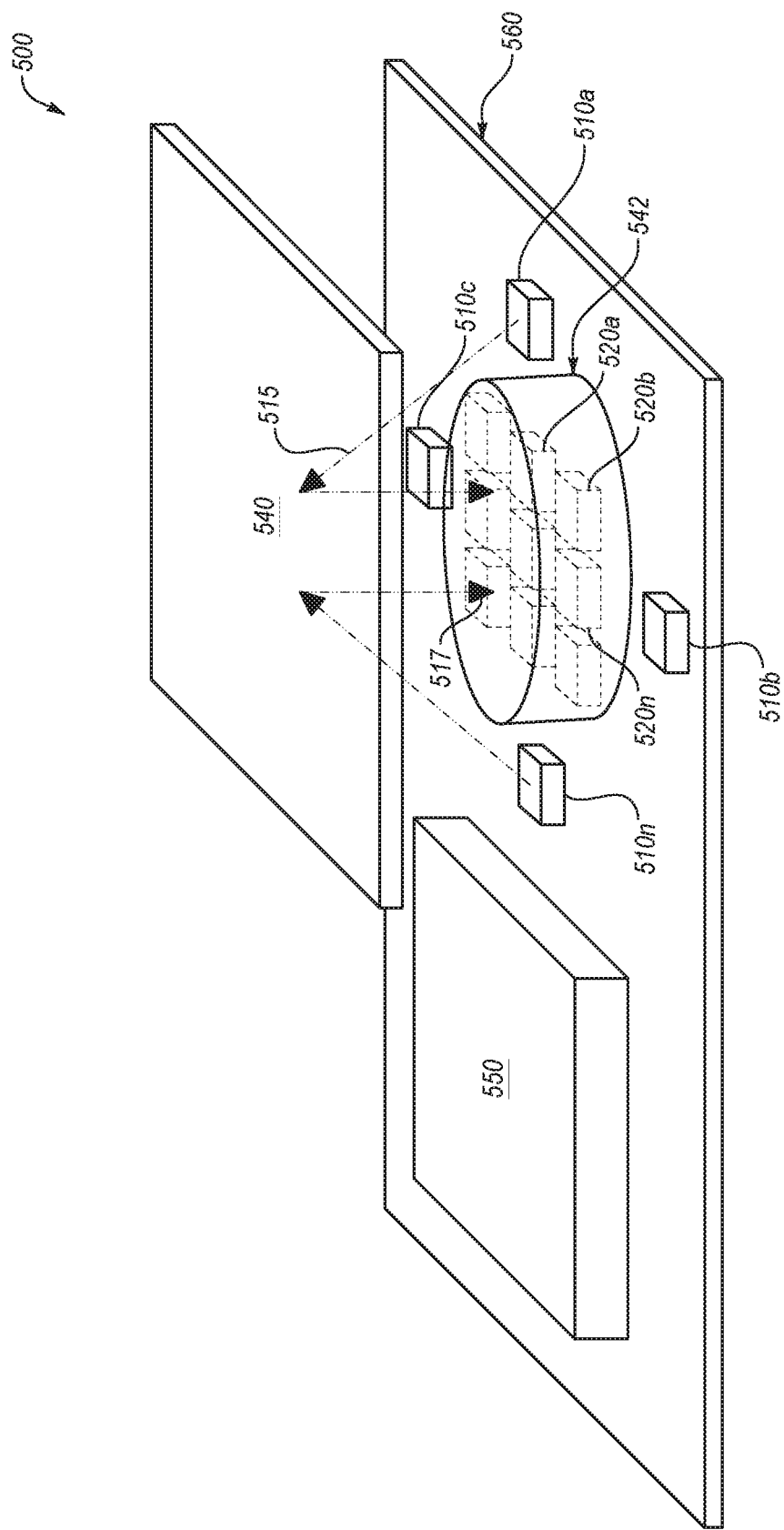
FIG. 5 illustrates another example system for imaging and/or analyzing a specimen.

FIG. 5 illustrates another example system 500 for imaging and/or analyzing a specimen, in accordance with one or more embodiments of the present disclosure. In some embodiments, the system 500 may be utilized in analyzing chemical compositions of bodily fluids, analytes, solutions, etc.

The system 500 may include a set of emitters 510 (such as the emitters 510a-510n) that may be similar or comparable to the emitters 110 of FIG. 1. The system 500 may additionally include a set of receivers 520 (such as the receivers 520a-520n) that may be similar or comparable to the receivers 120 of FIG. 1. The emitters 510 may emit EM radiation 515 towards an amplifying device 540 that may reflect the EM radiation back towards the specimen and the receivers 520b.

In some embodiments, the specimen may be located proximate another amplifying device 542 that may focus and/or amplify the EM radiation 517 as it interacts with or after it interacts with the specimen. For example, the amplifying device 542 may include a lens or other focusing device between the specimen (e.g., the bodily fluid or chemical solution) and the receivers 520.

As illustrated in FIG. 5, in some embodiments, the signals generated by the receivers 520 and/or the emitters 510 may be provided to a signal mixer unit 550. The signal mixer unit 550 may be similar or comparable to the signal mixer unit 150 of FIG. 1. The signal mixer unit 550 may extract markers from the signals.

In some embodiments, the system 500 may be implemented on an electronic circuit board 560, such as a printed circuit board (PCB). In these and other embodiments, an electrical connection may exist between one or more of the emitters 510 and/or the receivers 520 and the signal mixer unit 550 via the electronic circuit board 560.

Modifications, additions, or omissions may be made to the system 500 without departing from the scope of the present disclosure. For example, the system 500 may include a display, interface device, etc. for interacting with the signal mixer unit 550.

Figure 6:
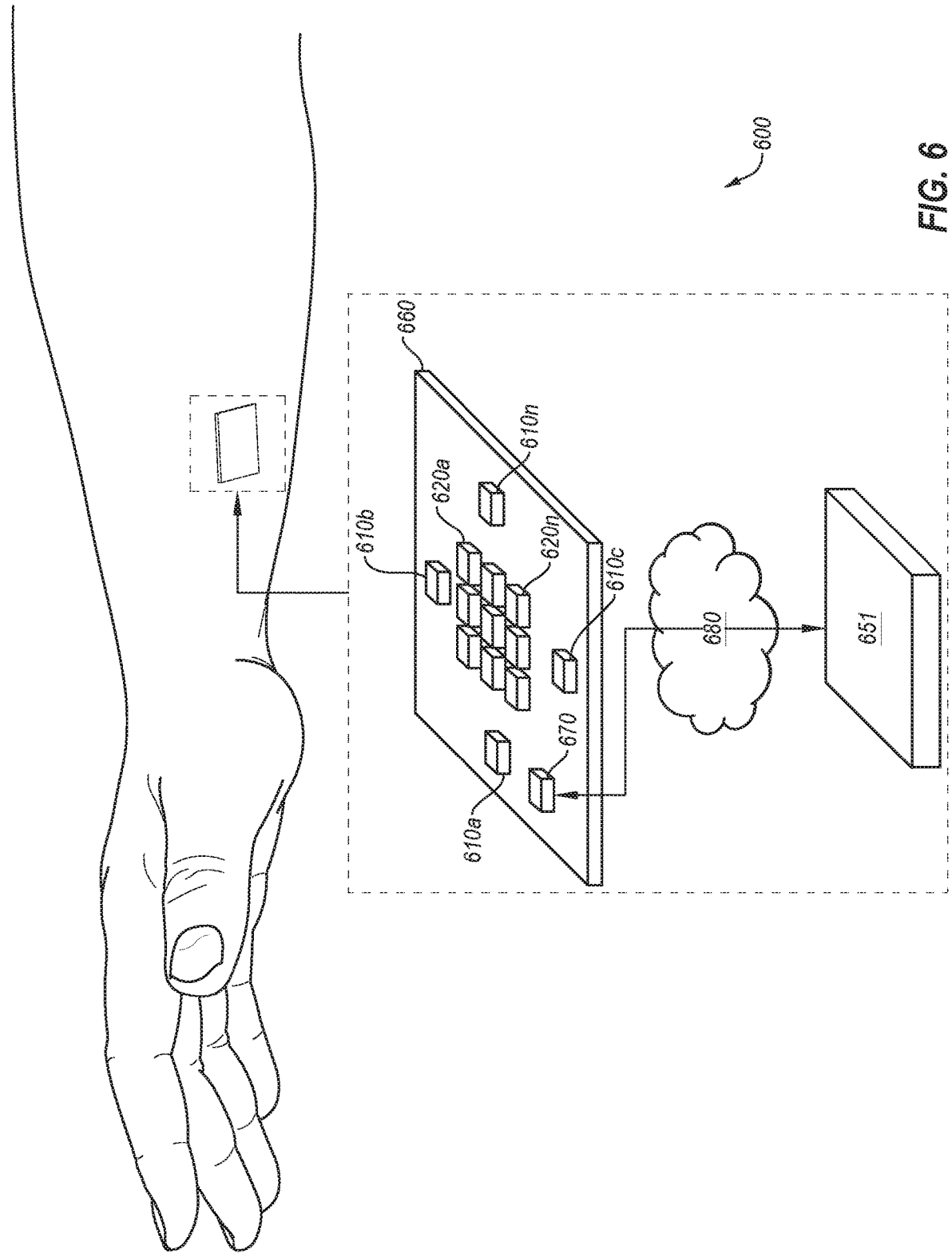
FIG. 6 illustrates an additional example system for imaging and/or analyzing a specimen.

FIG. 6 illustrates an additional example system 600 for imaging and/or analyzing a specimen, in accordance with one or more embodiments of the present disclosure. The system 600 may be implemented as a wearable device (such as a wrist-band, sticker, etc.) to continuously monitor skin of a user as the specimen to be analyzed.

The system 600 may include a set of emitters 610 (such as the emitters 610a-610n) that may be similar or comparable to the emitters 110 of FIG. 1. The system 600 may additionally include a set of receivers 620 (such as the receivers 620a-620n) that may be similar or comparable to the receivers 120 of FIG. 1. The emitters 610 may emit EM radiation towards the skin of the user (e.g., the specimen) that may scatter the EM radiation back towards the receivers 620b.

As illustrated in FIG. 6, in some embodiments, the signals generated by the receivers 620 and/or the emitters 610 may be provided to a communication device 670. The communication device may communicate the signals over a network 680 to signal mixer unit 651. The signal mixer unit 651 may be similar or comparable to the signal mixer unit 150 of FIG. 1. The signal mixer unit 651 may extract markers from the signals.

The network 680 may include any device, system, component, or combination thereof configured to provide communication between the communication device 670 and the signal mixer unit 651 and/or an associated device thereof. By way of example, the network 680 may include one or more wide area networks (WANs) and/or local area networks (LANs) that enable such communication. In some embodiments, the network 680 may include the Internet, including a global internetwork formed by logical and physical connections between multiple WANs and/or LANs. Alternately or additionally, the network 680 may include one or more cellular RF networks and/or one or more wired and/or wireless networks such as, but not limited to, 802.xx networks, Bluetooth access points, wireless access points, IP-based networks, or the like. The network 680 may also include servers that enable one type of network to interface with another type of network. In some embodiments, the network 680 may include device-to-device communication, such as IR communication, NFC, etc.

In some embodiments, the signal mixer unit 651 may be part of a mobile device or other electronic device of the user whose specimen is being analyzed. For example, the system 600 may include the cellular telephone or tablet of the user. In these and other embodiments, the system 600 may provide notifications, alarms, or other warnings or information to the user via the mobile device. In some embodiments, the signal mixer unit 651 may be part of an electronic device of a medical professional. For example, the signals may be communicated to an electronic device of a doctor or nurse treating the person whose skin is being monitored. In these and other embodiments, the signal mixer unit 651 may be located in a remote computing device, and notify the user and/or a medical professional based on the analysis by the signal mixer unit 651 triggering an alarm.

Modifications, additions, or omissions may be made to the system 600 without departing from the scope of the present disclosure.

Figure 7:
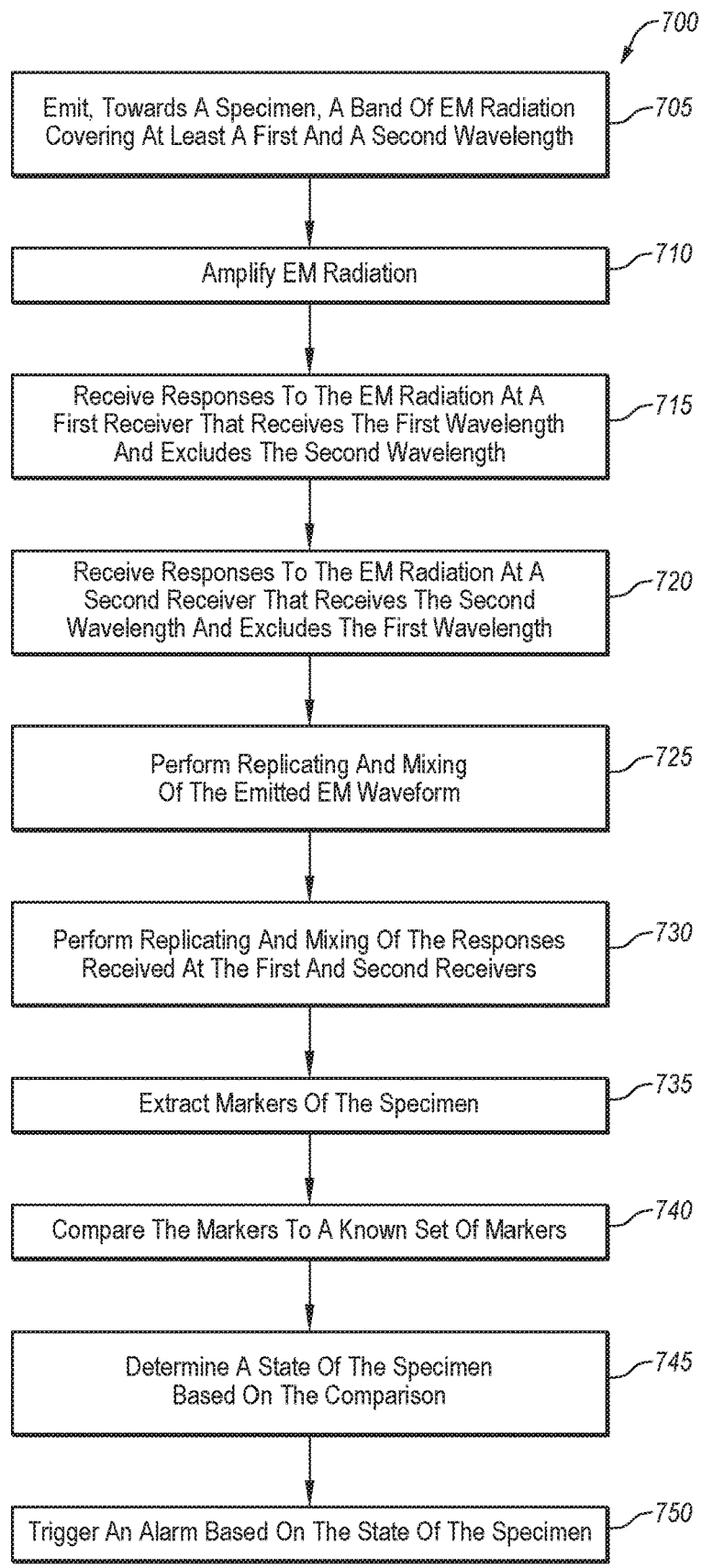
FIG. 7 illustrates a flow diagram of an example method of imaging and/or analyzing a specimen.

FIG. 7 illustrates a flow diagram of an example method 700 of imaging and/or analyzing a specimen, in accordance with one or more embodiments of the present disclosure.

At block 705, a band of EM radiation may be emitted towards a specimen, where the band of radiation includes at least a first wavelength and a second wavelength. For example, one or more emitters (such as the emitters 110 of FIG. 1, 210 of FIG. 2, 510 of FIG. 5, and/or 610 of FIG. 6) may emit EM radiation towards a specimen.

At block 710, the EM radiation may be amplified. For example, the EM radiation may be emitted towards a reflective material to direct the EM radiation towards the specimen and/or receivers. As another example, a lens or other focusing device may amplify the EM radiation after it has interacted with the specimen to facilitate an increase in a SNR associated with the EM radiation received at a receiver after interacting with the specimen.

At block 715, responses to the EM radiation may be received at a first receiver that is configured to receive the first wavelength and exclude the second wavelength. For example, a receiver (such as the receivers 120 of FIG. 1, 220 of FIG. 2, 520 of FIG. 5, and/or 620 of FIG. 6) may receive the responses to the EM radiation by the specimen. The responses received at the first receiver may be received after the emitted EM radiation has interacted with the specimen.

At block 720, responses to the EM radiation may be received at a second receiver that is configured to receive the second wavelength and exclude the first wavelength. The EM radiation received at the second receiver may be received after the emitted EM radiation has interacted with the specimen. In some embodiments, the EM radiation received at both the first receiver and the second receiver may have originated from the same emitter that emits the band of EM radiation covering both the first wavelength and the second wavelength. In these and other embodiments, such an arrangement may facilitate the simultaneous analysis of multiple markers and to thus account for interdependencies between the markers.

At block 725, replicating and mixing of the emitted EM waveforms may be performed. For example, the emitters may provide the EM waveforms used to emit the band of EM radiation to a signal mixer unit (such as the signal mixer unit 150 of FIG. 1, 250 of FIG. 2, 550 of FIG. 5, and/or 651 of FIG. 6) to perform replicating and mixing of the emitted EM waveforms.

At block 730, replicating and mixing of the responses received at the first and second receivers may be performed. For example, the signal mixer unit may receive the signals generated by the receivers and may mix and replicate the signals. In some embodiments, the replicating and mixing of the responses received at the receivers may also include the outputs of the replicating and mixing performed at the block 725 on the emitted EM waveforms.

At block 735, markers of the specimen may be extracted. For example, the output of the replicating and mixing at the block 730 may include one or more of the markers.

At block 740, the markers may be compared to a known set of markers. For example, the markers may be compared via table lookup operation or a database comparison to compare the markers to known markers of known states, conditions, concentrations, etc. of the parameters and/or markers being analyzed for the specimen.

At block 745, a state of the specimen may be determined and/or predicted based on the comparison performed at the block 740. For example, if the extracted markers are within a threshold amount, percentage, etc. of a known set of markers, the extracted markers may correspond to the same state as the known set of markers. Such determination may be based on multiple markers and their relationship to multiple sets of known markers.

At block 750, an alarm may be triggered based on the state of the specimen. For example, if it is determined that the state is outside of a normal state (e.g., the pallor of skin is beyond a threshold amount of paleness, a chemical compound like THC being searched for is found, etc.), the alarm may be triggered. The alarm may be in the form of an audible alert, a light that is illuminated, a communication sent to another electronic device, a notification or other software-based message that is triggered, etc.

Modifications, additions, or omissions may be made to the method 700 without departing from the scope of the present disclosure. For example, the operations may be performed in a differing order. As another example, additional operations may be added to, or performed in conjunction with the operations of the method 700. As an additional example, operations may be added, omitted, and/or performed simultaneously. As another example, various operations may be combined into a single operation, or a single operation may be divided into multiple operations.

Figure 8:
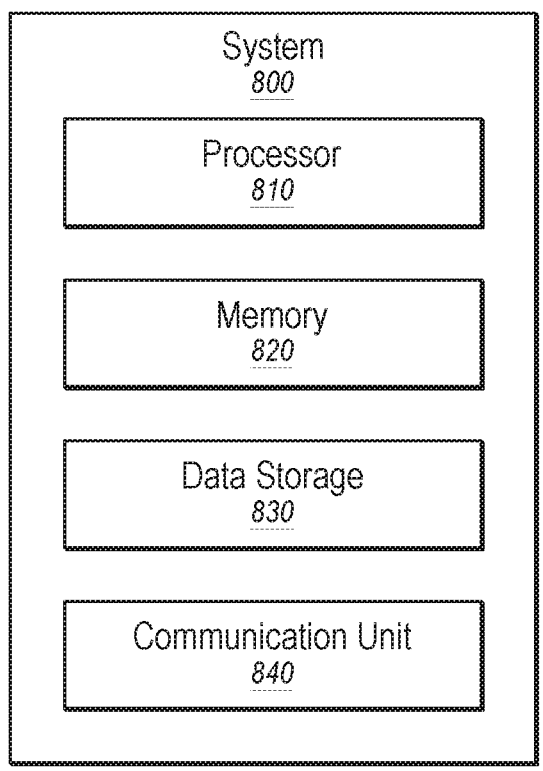
FIG. 8 illustrates an example computing system.

FIG. 8 illustrates an example computing system 800, according to at least one embodiment described in the present disclosure. The system 800 may include any suitable system, apparatus, or device configured to facilitate the imaging and/or analysis of a specimen. In some embodiments, any of the systems 100, 500 and/or 600 and/or portions or components thereof may be implemented as the computing system 800 illustrated in FIG. 8. The computing system 800 may include a processor 810, a memory 820, a data storage 830, and a communication unit 840, which all may be communicatively coupled. The data storage 830 may include various types of data, such as software projects, API documents, computer source code, etc.

Generally, the processor 810 may include any suitable special-purpose or general-purpose computer, computing entity, or processing device including various computer hardware or software modules and may be configured to execute instructions stored on any applicable computer-readable storage media. For example, the processor 810 may include a microprocessor, a microcontroller, a digital signal processor (DSP), an application-specific integrated circuit (ASIC), a Field-Programmable Gate Array (FPGA), or any other digital, analog, or optical circuitry configured to interpret and/or to execute program instructions and/or to process data.

Although illustrated as a single processor in FIG. 8, it is understood that the processor 810 may include any number of processors distributed across any number of network or physical locations that are configured to perform individually or collectively any number of operations described in the present disclosure. In some embodiments, the processor 810 may interpret and/or execute program instructions and/or process data stored in the memory 820, the data storage 830, or the memory 820 and the data storage 830. In some embodiments, the processor 810 may fetch program instructions from the data storage 830 and load the program instructions into the memory 820.

After the program instructions are loaded into the memory 820, the processor 810 may execute the program instructions, such as instructions to perform one or more operations of the method 700 of FIG. 7. For example, the processor 810 may obtain instructions regarding directing emitters to emit EM radiation at a broad band of frequencies of EM radiation, receive signals from receivers representing received EM radiation at specific frequencies after interacting with a specimen, and perform processing on the signals to extract markers from the subject, such as by reproducing and mixing various aspects or features of the signals to derive the markers.

The memory 820 and the data storage 830 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 810. In some embodiments, the computing system 800 may or may not include either of the memory 820 and the data storage 830.

By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 810 to perform a certain operation or group of operations.

The communication unit 840 may include any component, device, system, or combination thereof that is configured to transmit or receive information over a network. In some embodiments, the communication unit 840 may communicate with other devices at other locations, the same location, or even other components within the same system. For example, the communication unit 840 may include a modem, a network card (wireless or wired), an optical communication device, an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, or others), and/or the like. The communication unit 840 may permit data to be exchanged with a network and/or any other devices or systems described in the present disclosure. For example, the communication unit 840 may allow the system 800 to communicate with other systems, such as computing devices and/or other networks. As another example, the communication unit 840 may communicate with a separate processing device to perform the extraction of markers on received signals.

Modifications, additions, or omissions may be made to the system 800 without departing from the scope of the present disclosure. For example, the data storage 830 may be multiple different storage mediums located in multiple locations and accessed by the processor 810 through a network.

As indicated above, the embodiments described in the present disclosure may include the use of a special purpose or general purpose computer (e.g., the processor 810 of FIG. 8) including various computer hardware or software modules, as discussed in greater detail below. Further, as indicated above, embodiments described in the present disclosure may be implemented using computer-readable media (e.g., the memory 820 or data storage 830 of FIG. 8) for carrying or having computer-executable instructions or data structures stored thereon.

As used in the present disclosure, the terms "module" or "component" may refer to specific hardware implementations configured to perform the actions of the module or component and/or software objects or software routines that may be stored on and/or executed by general purpose hardware (e.g., computer-readable media, processing devices, or some other hardware) of the computing system. In some embodiments, the different components, modules, engines, and services described in the present disclosure may be implemented as objects or processes that execute on the computing system (e.g., as separate threads). While some of the systems and methods described in the present disclosure are generally described as being implemented in software (stored on and/or executed by general purpose hardware), specific hardware implementations or a combination of software and specific hardware implementations are also possible and contemplated. In this description, a "computing entity" may be any computing system as previously defined in the present disclosure, or any module or combination of modulates running on a computing system.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least,"

the term "includes" should be interpreted as "includes, but is not limited to," among others).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited in the present disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A method, comprising:
   emitting a band of electromagnetic (EM) radiation towards a specimen, the band covering at least a first and a second wavelength of EM radiation;
   receiving, at a first receiver configured to receive the first wavelength of EM radiation and exclude the second wavelength of EM radiation, responses to the EM radiation after the EM radiation interacts with the specimen;
   receiving, at a second receiver configured to receive the second wavelength of EM radiation and exclude the first wavelength of EM radiation, responses to the EM radiation after the EM radiation interacts with the specimen; and
   extracting a plurality of markers from a combination of first signals representative of the received responses at the first receiver and second signals representative of the received responses at the second receiver, the extracting including replicating and mixing the first signals and the second signals to extract the plurality of markers.

2. The method of claim 1, further comprising amplifying the responses to the EM radiation after the EM radiation interacts with the specimen such that the first receiver and the second receiver receive an amplification of the responses.

3. The method of claim 1, wherein the specimen includes at least one of human tissue or human bodily fluid, in vivo or in vitro.

4. The method of claim 1, wherein the markers indicate presence or absence of at least two compounds of interest.

5. The method of claim 1, wherein the markers indicate at least two of concentration of hemoglobin, concentration of deoxygenated hemoglobin, concentration of bilirubin, concentration of carotenes, concentration of eumelanin, pallor of skin, skin pigmentation, hormones, proteomes, primary metabolites, molecular conjugates, protein biomarkers, protein fragments, organic contaminants, inorganic contaminants, endogenous ions, heavy metals, and genes.

6. The method of claim 1, further comprising wirelessly transmitting the first signals and the second signals to a processing device to perform the extracting.

7. The method of claim 1, further comprising continuously monitoring the plurality of markers by repeatedly performing the emitting, the receiving, the receiving, and the extracting steps.

8. The method of claim 1, wherein the replicating and mixing includes:
   replicating each of the first signals and the second signals a plurality of times; and
   for each mixer unit, utilizing the replicated signals as input signals for the mixing, where the mixing utilizes a mixing function $f_j$:

$$f_j(x_1, x_2, \ldots, x_p) = a_1 x_1^{b_1} + a_2 x_2^{b_2} + \ldots + a_p x_p^{b_p}$$

where $x_i$ corresponds to an ith input signal, $a_i$ and $b_i$ are parameters corresponding to the ith input signal, and $f_j$ corresponds to the jth extracted marker.

9. The method of claim 1, further comprising comparing the plurality of markers to a known set of markers to predict a state of the specimen.

10. A system, comprising:
    an emitter configured to emit a band of radiation towards a specimen, the band including both a first wavelength of electromagnetic (EM) radiation and a second wavelength of EM radiation;

a first receiver configured to receive responses to the first wavelength of EM radiation after the first wavelength of EM radiation interacts with the specimen;

a second receiver configured to receive responses to the second wavelength of EM radiation after the second wavelength of EM radiation interacts with the specimen; and a signal mixer unit configured to extract a plurality of markers from a combination of first signals representative of the received responses at the first receiver and second signals representative of the received responses at the second receiver, the extracting including replicating and mixing the first signals and the second signals to extract the plurality of markers.

11. The system of claim 10, wherein the system is configured as a wearable and mobile device.

12. The system of claim 10, wherein the system includes a rechargeable battery to power at least the emitter and the signal mixer unit.

13. The system of claim 10, wherein the signal mixer unit includes one of an analog or digital processing device implemented via an electronic, optical, or chemical subsystem.

14. The system of claim 10, further comprising at least one additional emitter, the emitter and the at least one additional emitter arranged in an outside region surrounding where the first receiver and the second receiver are located.

15. The system of claim 10, further comprising an amplification device configured to amplify the first and the second responses to the EM radiation after the EM radiation interacts with the specimen and before the first response is received at the first receiver and before the second response is received at the second receiver.

16. The system of claim 15, wherein the amplification device is further configured to amplify the EM radiation before the EM radiation interacts with the specimen.

17. The system of claim 15, wherein the system is configured to extract the markers within eleven minutes of an initial emitting of the band of radiation towards the specimen.

18. The system of claim 10, further comprising:
a comparison device configured to compare the plurality of markers with a known set of markers to determine a state of the specimen; and
an alarm device configured to generate an alarm based on the state of the specimen.

19. A non-transitory computer-readable medium containing instructions that, when executed by a processor, are configured to cause a system to perform one or more operations, the operations comprising:

instruct an emitter to emit a band of electromagnetic (EM) radiation towards a specimen, the band including a first wavelength and a second wavelength of EM radiation;

receive, via a first receiver configured to receive the first wavelength of EM radiation and exclude the second wavelength of EM radiation, responses to the EM radiation after the EM radiation interacts with the specimen;

receive, via a second receiver configured to receive the second wavelength of EM radiation and exclude the first wavelength of EM radiation, responses to the EM radiation after the EM radiation interacts with the specimen; and extract a plurality of markers from a combination of first signals representative of the received responses at the first receiver and second signals representative of the received responses at the second receiver, the extracting including replicating and mixing the first signals and the second signals to extract the plurality of markers.

20. The computer-readable medium of claim 19, wherein the replicating and mixing includes:

replicating each of the first signals and the second signals a plurality of times; and for each mixer unit, utilizing the replicated signals as input signals for the mixing, where the mixing utilizes a mixing function $f_j$:

$$f_j(x_1, x_2, \ldots, x_p) = a_1 x_1^{b_1} + a_2 x_2^{b_2} + \ldots + a_p x_p^{b_p}$$

where $x_i$ corresponds to an ith input signal, $a_i$ and $b_i$ are parameters corresponding to the ith input signal, and $f_j$ corresponds to the jth extracted marker.

* * * * *